(12) United States Patent
Johnston

(10) Patent No.: US 7,061,612 B2
(45) Date of Patent: Jun. 13, 2006

(54) LED POLARIMETER

(75) Inventor: David W. Johnston, Kensington, NH (US)

(73) Assignee: Osram Sylvania Inc., Danvers, MA (US)

( * ) Notice: Subject to any disclaimer, the term of this patent is extended or adjusted under 35 U.S.C. 154(b) by 0 days.

(21) Appl. No.: 10/711,605

(22) Filed: Sep. 28, 2004

(65) Prior Publication Data

US 2006/0066853 A1    Mar. 30, 2006

(51) Int. Cl.
*G01J 4/00* (2006.01)

(52) U.S. Cl. ..................................... 356/364

(58) Field of Classification Search .............. None
See application file for complete search history.

(56) References Cited

U.S. PATENT DOCUMENTS 5,209,231 A * 5/1993 Cote et al. ............... 600/310
6,246,893 B1 * 6/2001 Gobeli ...................... 600/318
6,924,893 B1 * 8/2005 Oldenbourg et al. ........ 356/369
2003/0227622 A1 * 12/2003 Priestley ..................... 356/365
2005/0148876 A1 * 7/2005 Endoh et al. ............... 600/454
2005/0207943 A1 * 9/2005 Puzey ....................... 422/82.05

FOREIGN PATENT DOCUMENTS

JP    WO 2004/021884    *  3/2004

* cited by examiner

*Primary Examiner*—Tu T. Nguyen
(74) *Attorney, Agent, or Firm*—Robert F. Clark

(57) ABSTRACT

An LED polarimeter is described which is suitable for measuring the stress in photoelastic materials. The polarimeter comprises a sequential arrangement of an LED light source, a first polarizer, a ¼ wave plate, and a second polarizer substantially aligned along a central axis. The relatively monochromatic LED light source essentially eliminates errors caused by chromatic abberations and heat damage to the polarizing film. Preferably, the LED light source emits in the green region of the visible spectrum to take advantage of the sensitivity of the human eye to this part of the spectrum.

9 Claims, 1 Drawing Sheet

LED POLARIMETER

FIELD OF THE INVENTION

This invention is related to polarimeters and more particularly to Senarmont-compensator-type polarimeters.

BACKGROUND OF THE INVENTION

Polarimeters are used to view and quantitatively measure stress in glass and other photoelastic materials. When isotropic, photoelastic materials, such as glass and some plastics, are stressed, they become anisotropic. The anisotropy within the material makes the stressed areas birefringent. With a polarimeter, one can determine the degree of anisotropy by observing the degree birefringence. This can then be related qualitatively and quantitatively to the amount stress within the material.

Polarimeters generally consist of a light source, a first polarizer, a ¼ wave plate and a second rotatable polarizer. In order to observe the birefringence, a sample of the material is placed between the first polarizer and the ¼ wave plate. Any stress with a principal axis 45° to either polarizer will appear as a bright area in a dark background. The intensity of the bright area is proportional to the amount of stress. By rotating the second polarizer, the birefringence can be cancelled causing the bright area to become extinct (dark). The degrees of rotation can be converted to a measurement of the phase shift in the light (birefringence) by multiplying the dominant wavelength of light and dividing by 180°. This results in a measurement of the birefringence that can be converted into the stress intensity by dividing by the stress optical coefficient and the optical path length.

A common light source for a polarimeter is an incandescent lamp. Although this produces a smooth spectrum of white light, nearly 85% of the energy input to the lamp is converted to heat. This excessive heat causes damages to the polarizing film of the first polarizer which is adjacent to the lamp. Over a relatively short period, the damage to the film diminishes the ability to measure stress.

A second disadvantage with incandescent lamps and other white light sources is chromatic abberations. As the birefringence in the material increases, the longer, red wavelengths will resolve at different positions (degrees of rotation) of the second polarizer from the shorter, blue wavelengths. This creates two overlapping images which makes it increasingly difficult to properly resolve birefringence of >60 nm. The error in the measurement increases with the degree of birefringence. As a result, what should be a relatively simple and repeatable measurement becomes one requiring a great deal of skill and experience and exhibiting a high degree of variation from one operator to another.

Some polarimeters use compact fluorescent lamps to diminish the damage to the polarizing film from heat. However, this greatly increases chance for chromatic abberations. When a polarimeter lamp fails, it must be replaced with a reasonably exact duplicate otherwise the difference in the emission spectrum will shift the calibration of the polarimeter. In the case of fluorescent lamps, it is easy to make a mistake since the emission spectrum of a fluorescent lamp is a function of the phosphors used in its manufacture, e.g., there are several "colors" of white for commercial fluorescent lamps. Likely, the operator will be unaware of the color shift of the lamp and therefore not able to compensate for it.

Thus, it would be an advantage to have a light source for a polarimeter which would overcome these difficulties.

SUMMARY OF THE INVENTION

It has been discovered that the disadvantages of the prior art may be essentially eliminated by using an LED light source. In particular, the LED source is relatively monochromatic which essentially eliminates errors which were caused by chromatic abberations. Furthermore, the LED light source is an efficient, low power device that generates only a minimal amount of heat so that there is no damage to the polarizing film. A typical LED device used in this invention consumes only 6 watts of power compared to 60–100 watts for an incandescent source and roughly 25 watts for a compact fluorescent source. Moreover, LEDs have such long lifetimes, >60,000 hours, that replacement may not be required.

The LED polarimeter of this invention comprises a sequential arrangement of an LED light source, a first polarizer, a ¼ wave plate, and a second polarizer substantially aligned along a central axis. The orientation of the first polarizer to the ¼ wave plate is fixed and the second polarizer is rotatable about the central axis. In a preferred embodiment, the LED light source emits in the green wavelength region from about 510 nm to about 540 nm. The human eye is particularly sensitive to green light which makes the analysis easier, and commercially available optics tend to be optimized for the green portion of the visible spectrum.

An additional benefit of the LED light source is that its compact, lightweight design together with its low power consumption allows for the construction of a smaller, portable instrument. For example, one commercially available polarimeter has an 8-inch diameter base, is 11 inches tall and weighs 11 pounds whereas one embodiment of the polarimeter of this invention has a 6×6 inch base, is 8 inches tall and weighs only 5 pounds.

DETAILED DESCRIPTION OF THE INVENTION

Figure 1:
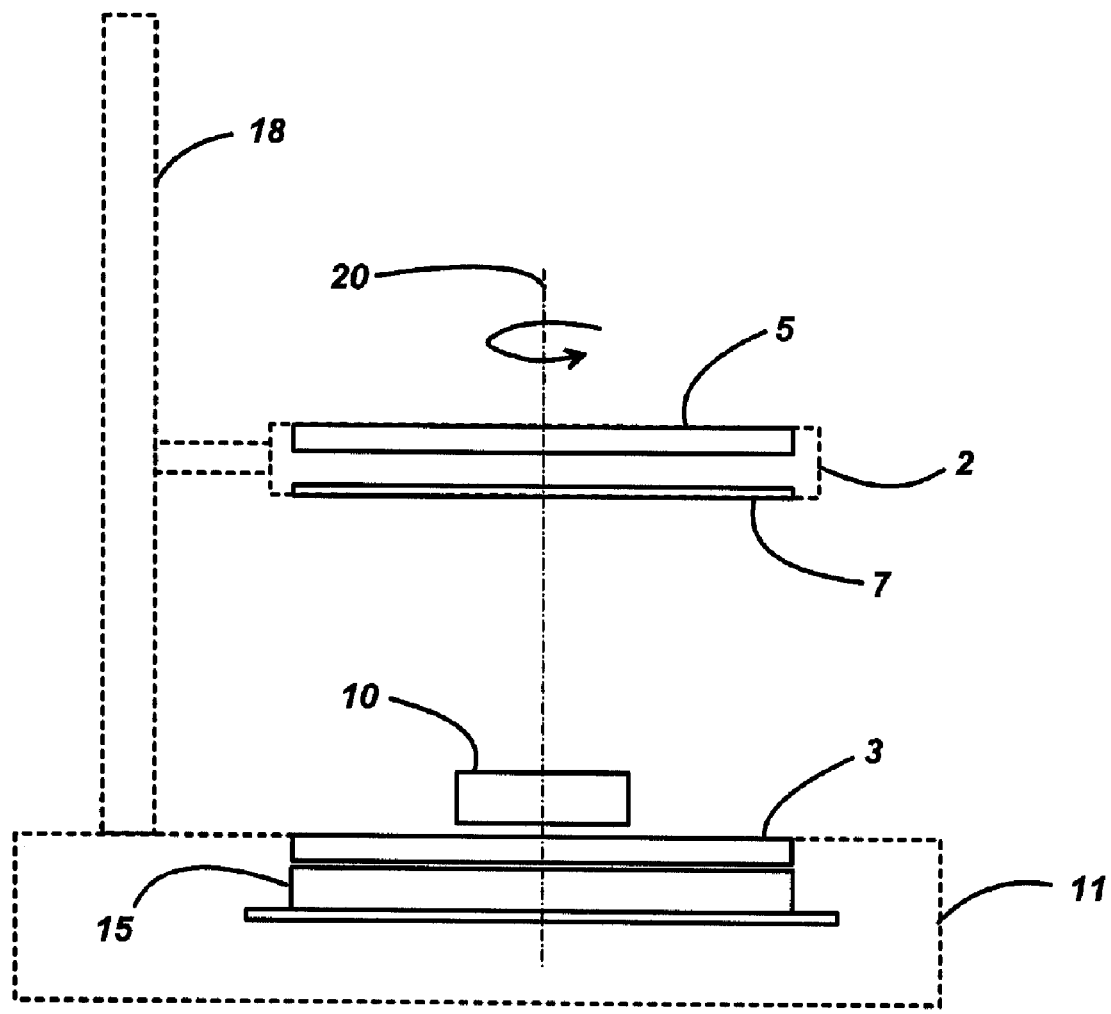
FIG. 1 is a schematic view of the LED polarimeter of this invention.

For a better understanding of the present invention, together with other and further objects, advantages and capabilities thereof, reference is made to the following disclosure and appended claims taken in conjunction with the above-described drawing.

Referring to FIG. 1, there is shown a schematic view of the LED polarimeter of this invention. The LED light source 15 is located adjacent to and below first polarizer 3. A ¼ wave plate 7 is suspended over the first polarizer 3 and below second polarizer 5. The supporting structure (shown in dotted-line contour) comprises base 11, vertical support 18 and adjustable holder 2. Generally, the LED source 15 and first polarizer 3 are supported and attached to base 11 which is connectable to or contains a source of electric power. The ¼ wave plate 7 and second polarizer 5 are located in the adjustable holder 2 which is attached to vertical support 18 in a manner which allows for vertical movement of the holder 2 along the central axis 20.

The LED light source 15, the ¼ wave plate 7 and the first and second polarizers 3, 5 are substantially aligned along central axis 20. Material sample 10 is placed between the first polarizer 3 and ¼ wave plate 7 in order to measure its birefringent properties.

The first and second polarizers 3, 5 are made of a polarizing film, preferably with an extinction ratio of about 10,000:1 or greater. The first polarizer 3 is held in position by base 11 and the ¼ wave plate is held in position by holder 2 such that the orientation of the first polarizer 3 is fixed with respect to the ¼ wave plate 7. The second polarizer 5 is rotatable about central axis 20 and has indicia suitable for determining the degree of rotation.

The LED light source 15 preferably yields a generally uniform illumination field. An example of a suitable LED light source is OSRAM Opto Semiconductors' MARKERlight No. OS-ML02A-T. This flat device uses 40 green-emitting LEDs (528 nm) to edge light a printed screen. This arrangement produces an even 2×2 inch field of illumination at about 1200 cd/m$^2$. When used in combination with the other components of the polarimeter, this makes for a very dark background and a very bright subject which greatly facilitates the measurement.

While there have been shown and described what are present considered to be the preferred embodiments of the invention, it will be apparent to those skilled in the art that various changes and modifications can be made herein without departing from the scope of the invention as defined by the appended claims.

What is claimed is:

1. A polarimeter comprising:
   a sequential arrangement of an LED light source, a first polarizer, a material sample, a ¼ wave plate, and a second polarizer substantially aligned along a central axis;
   the orientation of the first polarizer to the ¼ wave plate being fixed;
   the second polarizer being rotatable about the central axis; and
   the second polarizer and the ¼ wave plate being mounted in a holder that is moveable along the central axis in order to change a distance between the holder and the first polarizer.

2. The polarimeter of claim 1 wherein the LED light source has an emission maximum at a wavelength from about 510 nm to about 540 nm.

3. The polarimeter of claim 1 wherein the LED light source is comprised of multiple LEDs arranged to provide an even illumination field.

4. The polarimeter of claim 2 wherein the LED light source emits at 528 nm.

5. The polarimeter of claim 1 wherein the first polarizer comprises a polarizing film.

6. The polarimeter of claim 5 wherein the polarizing film has an extinction ratio of about 10,000:1 or greater.

7. The polarimeter of claim 6 wherein the LED light source has an emission maximum at a wavelength from about 510 nm to about 540 nm.

8. The polarimeter of claim 7 wherein the LED light source is comprised of multiple LEDs arranged to provide an even illumination field.

9. The polarimeter of claim 1 wherein the second polarizer has indicia for determining the degree of rotation.

* * * * *